(12) United States Patent  
Cheon et al.

(10) Patent No.: US 8,801,955 B2  
(45) Date of Patent: Aug. 12, 2014

(54) WATER-SOLUBLE NANOPARTICLES STABILIZED WITH MULTI-FUNCTIONAL GROUP LIGANDS AND METHOD OF PREPARATION THEREOF

(75) Inventors: Jin-Woo Cheon, Seoul (KR); Young-Wook Jun, Goyang-si (KR); Jin-Sil Choi, Daegu (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 13/550,082

(22) Filed: Jul. 16, 2012

(65) Prior Publication Data

US 2013/0020526 A1    Jan. 24, 2013

Related U.S. Application Data

(62) Division of application No. 11/571,397, filed as application No. PCT/KR2004/002509 on Sep. 30, 2004, now abandoned.

(30) Foreign Application Priority Data

Sep. 3, 2004    (KR) .................. 10-2004-0070304

(51) Int. Cl.
| | | |
|---|---|---|
| *B22F 3/00* | (2006.01) | |
| *C04B 35/64* | (2006.01) | |
| *H01F 1/04* | (2006.01) | |
| *C07F 15/00* | (2006.01) | |
| *C07C 43/00* | (2006.01) | |
| *A61K 38/00* | (2006.01) | |
| *C07K 16/00* | (2006.01) | |
| *C12P 21/08* | (2006.01) | |
| *C08F 26/00* | (2006.01) | |
| *C08F 126/00* | (2006.01) | |
| *C08F 226/00* | (2006.01) | |
| *C08L 67/00* | (2006.01) | |
| *C08L 77/00* | (2006.01) | |
| *C08G 63/00* | (2006.01) | |
| *A61K 49/18* | (2006.01) | |
| *A61K 47/48* | (2006.01) | |
| *B82Y 5/00* | (2011.01) | |

(52) U.S. Cl.
CPC ....... *A61K 47/48861* (2013.01); *A61K 49/1866* (2013.01); *B82Y 5/00* (2013.01); *A61K 49/1839* (2013.01); *A61K 49/1875* (2013.01); *A61K 47/48884* (2013.01); *A61K 49/1836* (2013.01); *Y10S 977/811* (2013.01); *Y10S 977/81* (2013.01); *Y10S 977/773* (2013.01); *Y10S 977/896* (2013.01); *Y10S 977/795* (2013.01)

USPC .................. 252/62.55; 525/326.7; 525/328.2; 525/330.4; 525/418; 525/420; 525/237; 525/450; 525/461; 525/329.5; 525/538; 556/138; 530/326; 530/327; 530/391.3; 568/623; 977/811; 977/810; 977/773; 977/896; 977/795

(58) Field of Classification Search
None
See application file for complete search history.

(56) References Cited

U.S. PATENT DOCUMENTS

| | | |
|---|---|---|
| 4,452,773 A | 6/1984 | Molday |
| 4,554,088 A | 11/1985 | Whitehead et al. |
| 4,554,098 A | 11/1985 | Klisch et al. |
| 4,795,998 A | 1/1989 | Dunbar et al. |
| 5,262,176 A | 11/1993 | Palmacci et al. |
| 5,411,730 A | 5/1995 | Kirpotin et al. |
| 5,508,164 A | 4/1996 | Kausch et al. |
| 5,665,582 A | 9/1997 | Kausch et al. |
| 6,262,129 B1 | 7/2001 | Murray et al. |
| 6,274,121 B1 | 8/2001 | Pilgrimm |
| 6,333,110 B1 | 12/2001 | Barbera-Guillem |
| 6,452,763 B1 | 9/2002 | Gill |
| 6,530,944 B2 | 3/2003 | West et al. |
| 6,548,264 B1 | 4/2003 | Tan et al. |
| 6,638,494 B1 | 10/2003 | Pilgrimm |
| 6,649,138 B2 * | 11/2003 | Adams et al. ................. 423/403 |
| 6,767,635 B1 * | 7/2004 | Bahr et al. .................... 428/402 |
| 6,855,749 B1 | 2/2005 | Yadav et al. |
| 6,940,277 B2 | 9/2005 | Fries |

| | | | |
|---|---|---|---|
| 6,944,939 | B2 | 9/2005 | Guo et al. |
| 7,459,145 | B2 * | 12/2008 | Bao et al. .............. 424/9.32 |
| 2002/0120165 | A1 | 8/2002 | Zaworotko et al. |
| 2003/0092029 | A1 | 5/2003 | Josephson et al. |
| 2003/0133232 | A1 | 7/2003 | Li et al. |
| 2003/0185757 | A1 | 10/2003 | Kresse et al. |
| 2003/0190471 | A1 | 10/2003 | Carpenter et al. |
| 2004/0058457 | A1 | 3/2004 | Huang et al. |
| 2004/0077844 | A1 | 4/2004 | Jacobson et al. |
| 2004/0247503 | A1 | 12/2004 | Hyeon |
| 2005/0130167 | A1 | 6/2005 | Bao et al. |
| 2005/0165120 | A1 | 7/2005 | Kumar et al. |
| 2005/0215687 | A1 | 9/2005 | Hatton et al. |
| 2006/0177879 | A1 | 8/2006 | Mayes et al. |

FOREIGN PATENT DOCUMENTS

| | | |
|---|---|---|
| KR | 10-1998-0705262 | 10/1999 |
| KR | 10-2003-0096097 | 12/2003 |
| KR | 10-2005-0048715 | 5/2005 |
| KR | 10-2006-0008234 | 1/2006 |
| KR | 10-0604976 | 7/2006 |
| KR | 10-0652251 | 11/2006 |
| WO | WO 03031323 A1 * | 4/2003 |
| WO | 2003-072247 | 9/2003 |
| WO | 2004-110619 | 12/2004 |

OTHER PUBLICATIONS

International Search Report dated Jun. 3, 2005, for Application No. PCT/KR2004/002509.

Written Opinion dated Jun. 3, 2005, for Application No. PCT/KR2004/002509.

International Search Report dated Apr. 30, 2007, for Application No. PCT/KR2007/001001.

Hong et al., "In situ observation of place exchange reactions of gold nanoparticles. Correlation of monolayer structure and stability" Chem. Commun., 2006, 2197-2199, The Royal Society of Chemistry.

Mohr et al. "Initiation of shape-memory effect by inductive hearing of magnetic nanoparticles in thermoplastic polymers" Proceedings of National Academy of Science USA, Mar. 7, 2006, vol. 103, p. 3540-3545.

Sun et al., "Size-Controlled Synthesis of Magnetite Nanoparticles" J. Am. Chem. Soc. 2002, col. 124, p. 8204-8205, American Chemical Society.

Jana et al., "Size- and Shape-Controlled Magnetic (Cr, Mn, Fe, Co, Ni) Oxide Nanocrystals via a Simple and General Approach" Chem. Matter. 2004, col. 16, p. 3931-3935, American Chemical Society.

Wikipedia printout regarding "Lipid", printed on Jun. 27, 2012.

Gupta et al., "Synthesis and surface engineering of iron oxide nanoparticle for biomedical applications" J. Biomaterials 26, pp. 3995-4021, 2005, Elsevier Ltd.

Mornet et al., "A method for synthesis and functionalization of ultrasmall superparamagnetic covalent carriers based on maghemite and dextran" J. Magnetism Magnetic Mater 293, pp. 127-134, 2005, Elsevier B.V.

Da Silva et al., "Study of the interactions between the surface chemisorbed layer and the surrounding media in magnetite-coated nanoparticles using Raman spectroscopy" J. Magnetism Magnetic Mater 226-230, p. 1890-1892, 2001, Elsevier B. V.

Nobs et al., "Current Methods for Attaching Targeting Ligands to Liposomes and Nanoparticles" J. Pharm. Sci., vol. 93, No. 8, pp. 1980-1992, Aug. 2004, Wiley-Liss, Inc. and the American Pharmacists Association.

Robinson et al., "DNA-Functionalized MFe$_2$O$_2$ (M = Fe, Co, or Mn) Nanoparticles and Their Hybridization to DNA-Functionalized Surfaces" Langmuir, 21, pp. 3096-3103, 2005, American Chemical Society.

* cited by examiner

*Primary Examiner* — Cherie M Stanfield

(74) *Attorney, Agent, or Firm* — Swanson & Bratschun, L.L.C.

(57) ABSTRACT

Disclosed are water-soluble nanoparticles. The water-soluble nanoparticles are each surrounded by a multifunctional group ligand including an adhesive region, a cross linking region, and a reactive region. In the water-soluble nanoparticles, the cross-linking region of the multifunctional group ligand is cross-linked with another cross-linking region of a neighboring multifunctional group ligand. Furthermore, the present invention provides a method of producing water-soluble nanoparticles, which includes (1) synthesizing water-insoluble nanoparticles in an organic solvent, (2) dissolving the water insoluble nanoparticles in a first solvent and dissolving water-soluble multifunctional group ligands in a second solvent, (3) mixing the two solutions from the step (2) to substitute surfaces of the water-insoluble nanoparticles with the multifunctional group ligands and dissolving a mixture in an aqueous solution to conduct a separation process, and (4) cross-linking the substituted multifunctional group ligands with each other.

25 Claims, 12 Drawing Sheets water-insoluble nanoparticles which are each surrounded by the organic surface stabilizer sythesized in the step(1)

water-soluble nanoparticles substituted with multifunctional group ligands

WATER-SOLUBLE NANOPARTICLES STABILIZED WITH MULTI-FUNCTIONAL GROUP LIGANDS AND METHOD OF PREPARATION THEREOF

CROSS-REFERENCE TO RELATED APPLICATIONS

The present application is a divisional application of U.S. patent application Ser. No. 11/571,397, filed Dec. 28, 2006, which is a national stage application under 35 U.S.C. §371 of PCT Application No. PCT/KR2004/002509 having an international filing date of Sep. 30, 2004, which claims priority to Korean Application Serial No. 10-2004-0070304, filed Sep. 3, 2004, all of which are expressly incorporated herein by reference in their entireties.

TECHNICAL FIELD

The present invention relates, in general, to water-soluble nanoparticles and, more particularly, to water-soluble nanoparticles, which are each surrounded by a multifunctional group ligand ($L_I$-$L_{II}$-$L_{III}$) including an adhesive region ($L_I$), a cross-linking region ($L_{II}$), and a reactive region ($L_{III}$), and in which the cross-linking region of the multifunctional group ligand is cross-linked with another cross-linking region of a neighboring multifunctional group ligand.

Furthermore, the present invention pertains to a method of producing water-soluble nanoparticles, which includes (1) synthesizing water-insoluble nanoparticles in an organic solvent, (2) dissolving the water-insoluble nanoparticles in a first solvent and dissolving water-soluble multifunctional group ligands in a second solvent, (3) mixing two solutions in the step (2) to substitute surfaces of the water-insoluble nanoparticles with the multifunctional group ligands and dissolving a mixture in an aqueous solution to conduct a separation process, and (4) cross-linking the substituted multifunctional group ligands with each other.

BACKGROUND ART

Used to adjust and control a substance at an atomic or molecular level, nanotechnology is suitable to create novel substances and materials, and applied to various fields, such as electronic, material, communication, mechanical, medical, agricultural, energy, and environmental fields.

Currently, development of various types of nanotechnologies is in progress, and the nanotechnology is usually classified into the following three categories. The first category relates to a technology to synthesize ultrafine novel substances and matter using a nano-material. The second category relates to a technology to produce a device which assures predetermined functions by combining or arranging nano-sized materials. The third category relates to a technology to apply a nanotechnology, which is called a nano-bio, to bioengineering.

Particularly, in nano-bio fields, nanoparticles are used to specifically kill cancer cells, boost an immune reaction, fuse cells, deliver genes or drugs, conduct diagnosis and the like. In order to apply the nanoparticles to the above applications, the nanoparticles must have portions, to which active components are capable of adhering, and must be stably delivered and dispersed in vivo, that is, in a water-soluble environment. Many technologies have lately been developed to satisfy such conditions.

U.S. Pat. No. 6,274,121 discloses paramagnetic nanoparticles including metals, such as iron oxides, to which inorganic materials, having binding sites that are capable of being coupled with tissue-specific binding substances and diagnostically or pharmaceutically active materials, adhere.

U.S. Pat. No. 6,638,494 pertains to paramagnetic nanoparticles containing metals, such as iron oxides, and discloses a method of preventing nanoparticles from cohering and precipitating in the gravity or magnetic fields, in which specific carboxylic acid adheres to surfaces of the nanoparticles. Examples of the above carboxylic acid include aliphatic dicarboxylic acid, such as maleic acid, tartaric acid, and glucaric acid, or aliphatic polycarboxylic acid, such as citric acid, cyclohexane, and tricarboxylic acid.

U.S. Pat. No. 6,649,138 discloses a method of improving the water-soluble property of nanoparticles, in which a multiply amphiphilic dispersant layer is formed on surfaces of the hydrophobic nanoparticles having semiconductor or metal materials. The multiply amphiphilic dispersant is exemplified by (1) a hydrophobic backbone having hydrophilic branched chains, (2) a hydrophilic backbone having hydrophobic branched chains, or (3) a hydrophobic or hydrophilic backbone simultaneously having hydrophilic and hydrophobic branched chains.

U.S. Patent Application No. 2004/0033345 discloses a method of capsulizing nanoparticles, in which hydrophobic ligand layers are formed around metals or semiconductors, using micelles to dissolve the nanoparticles in an aqueous solution. At this time, the micelles consist of hydrophilic shells and hydrophobic cores.

U.S. Patent Application No. 2004/0058457 suggests functional nanoparticles which are surrounded by monolayers, and in which bifunctional peptides adhere to the monolayers and various biopolymers including DNA and RNA are bound to the peptides.

However, the water-soluble nanoparticles produced according to the above method, have the following disadvantages. In U.S. Pat. Nos. 6,274,121, and 6,638,494, and U.S. Patent Application No. 2004/0058457, the nanoparticles are synthesized in aqueous solution. In such a case, it is difficult to control the sizes of the nanoparticles, and the synthesized nanoparticles have a nonuniform size distribution. Furthermore, since they are synthesized at low temperatures, crystallinities of the nanoparticles are low and non-stoichiometric compounds are apt to be generated. Additionally, surfaces of the nanoparticles are coated with a monomolecular surface stabilizer, but bonding strengths between the stabilizer and the nanoparticles are not high, and thus, the nanoparticles are less stable in aqueous solution. The water-soluble nanoparticles of U.S. Pat. No. 6,649,138 and U.S. Patent Application No. 2004/0033345 are surrounded by amphiphilic polymers, thus having significantly increased diameters in comparison with inorganic nanoparticles. Further, successful application examples of these nanoparticles are limited to semiconductor nanoparticles.

DISCLOSURE OF THE INVENTION

Accordingly, an object of the present invention is to provide water-soluble nanoparticles which are highly stable in aqueous solution and have low toxicity to living bodies, thereby being applied to various fields, such as bio diagnosis and treatment, and electronic materials, and a method of preparation thereof.

In order to accomplish the above object, the present inventors added multifunctional group ligands, each of which includes (a) an adhesive region bonded to nanoparticles, (b) a cross-linking region stabilizing the nanoparticles in an aqueous solution, and (c) a reactive region capable of being bonded to active components, to the nanoparticles gained from an organic solvent, thereby producing nanoparticles which are stable in aqueous solution and are capable of being bonded to various active components.

The present invention provides water-soluble nanoparticles, which are each surrounded by a multifunctional group ligand including an adhesive region, a cross-linking region, and a reactive region, and in which the cross-linking region of the multifunctional group ligand is cross-linked with another cross-linking region of a neighboring multifunctional group ligand.

Furthermore, the present invention provides a method of producing water-soluble nanoparticles, which includes (1) synthesizing water-insoluble nanoparticles in an organic solvent, (2) dissolving the water-insoluble nanoparticles in a first solvent and dissolving water-soluble multifunctional group ligands in a second solvent, (3) mixing two solutions in the step (2) to substitute surfaces of the water-insoluble nanoparticles with the multifunctional group ligands and dissolving a mixture in an aqueous solution to conduct a separation process, and (4) cross-linking the substituted multifunctional group ligands with each other.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
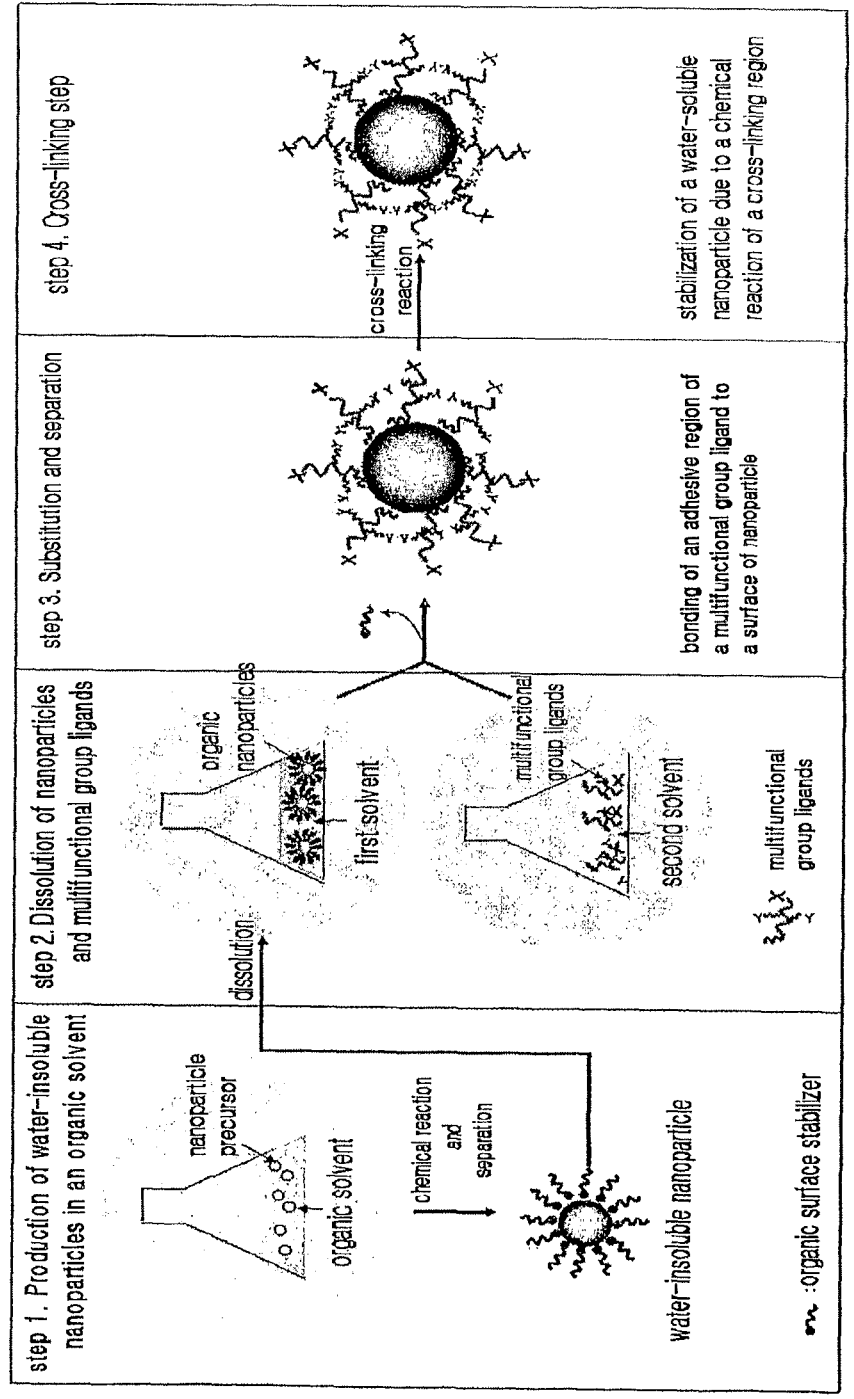
FIG. 1 illustrates the production of water-soluble nanoparticles from water-insoluble nanoparticles according to the present invention.
Figure 2:
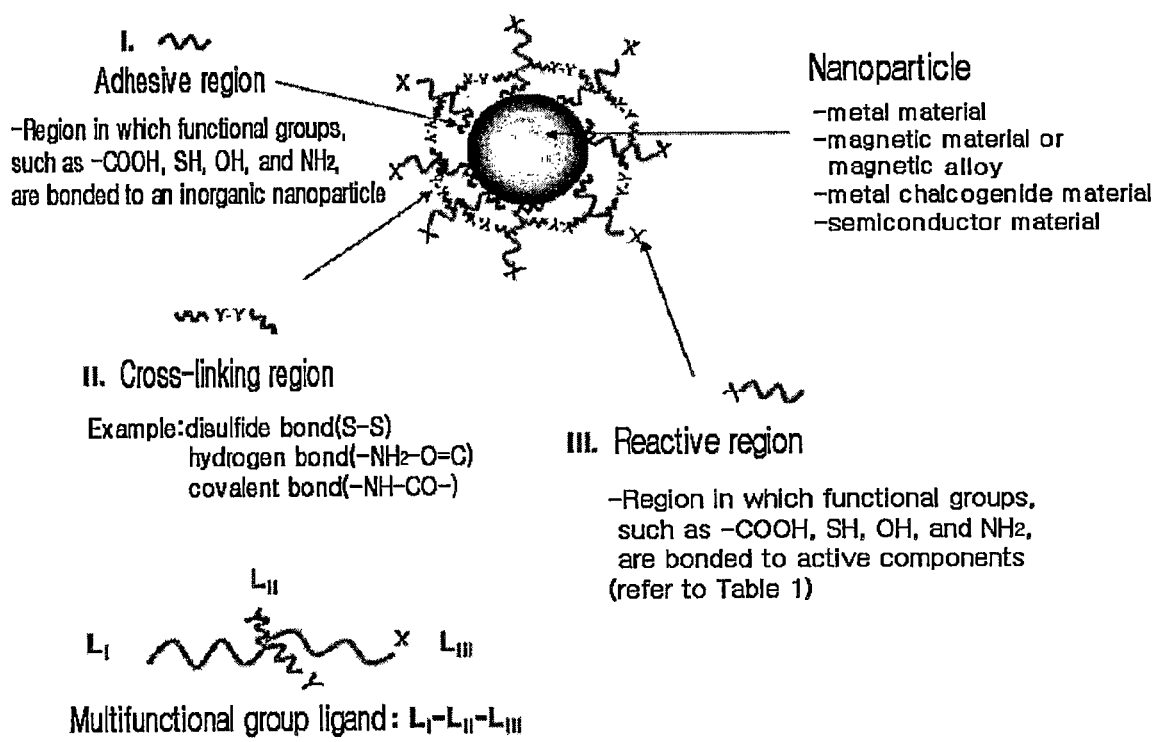
FIG. 2 schematically illustrates the water-soluble nanoparticles according to the present invention.

In the specification of the present invention, "nanoparticles" means particles which each include a metal material, a metal chalcogenide, a magnetic material, a magnetic alloy, a semiconductor material, or a multicomponent mixed structure and each of which has a diameter of 1-1000 nm, and preferably 2-100 nm.

In the specification of the present invention, "water-insoluble nanoparticles" means nanoparticles surrounded by a hydrophobic surface stabilizer, which may be produced through a chemical reaction of a nanoparticle precursor in an organic solvent, containing a typical surface stabilizer, so as to have excellent crystallinity and desired size, shape, and composition. The "surface stabilizer" means organic functional molecules capable of stabilizing a state and a size of the nanoparticle, and representative examples include a surfactant.

Regarding "water-soluble nanoparticles" according to the present invention, a water-soluble multifunctional group ligand layer is formed instead of the hydrophobic surface stabilizer on surfaces of the water-insoluble nanoparticles. The multifunctional group ligands are cross-linked with each other, and thus, the water-soluble nanoparticles can be stably dissolved and dispersed in an aqueous solution. In detail, the water-soluble nanoparticles are surrounded by the multifunctional group ligands, each of which includes an adhesive region, a cross-linking region, and a reactive region. The cross-linking regions of the multifunctional group ligands are cross-linked with other cross-linking regions of neighboring multifunctional group ligands.

The water-soluble nanoparticles according to the present invention may be provided in various forms which depend on the type of metal, metal chalcogenide, magnetic material, magnetic alloy, semiconductor material or multicomponent mixed structure, and multifunctional group ligand.

Examples of the metal include Pt, Pd, Ag, Cu, Au, Ru, Rh, and Os, and the metal chalcogenide is exemplified by $M_xE_y$ (M=Ti, V, Cr, Mn, Fe, Co, Ni, Cu, Zr, Mo, Ru, Rh, Ag, W, Re, Ta, Zn; E=O, S, Se, $0<x\leq3$, $0<y\leq5$), BaSr$_x$Ti$_{1-x}$O$_3$, PbZr$_x$Ti$_{1-x}$O$_3$ ($0\leq x\leq1$), and SiO$_2$. Examples of the magnetic material include Co, Mn, Fe, Ni, Gd, MM'$_2$O$_4$, and M$_x$O$_y$ (M or M'=Co, Fe, Ni, Mn, Zn, Gd, Cr, $0<x\leq3$, $0<y\leq5$), and the magnetic alloy is exemplified by CoCu, CoPt, FePt, CoSm, NiFe, CoAu, CoAg, CoPtAu, CoPtAg and NiFeCo.

Furthermore, examples of the semiconductor material may include a semiconductor material consisting of elements selected from group II (Zn, Cd, Hg) and elements selected from group VI (O, S, Se), a semiconductor material consisting of elements selected from group III (B, Al, Ga, In) and elements selected from group V (P, As, Sb), a semiconductor material consisting of group IV (Si, Ge, Pb, Sn), a semiconductor material consisting of elements selected from group IV (Si, Ge) and elements selected from group VI (O, S, Se), or a semiconductor material consisting of elements selected from group V (P, As, Sb, Bi) and elements selected from group VI (O, S, Se).

The "multicomponent mixed structure" is a particle including two or more components selected from the group consisting of metal, metal chalcogenide, magnetic material, magnetic alloy, and semiconductor material, and representative examples in shape are a core-shell and a bar code.

In the specification of the present invention, the "multifunctional group ligand ($L_I$-$L_{II}$-$L_{III}$)" means a material including (a) an adhesive region ($L_I$), (b) a cross-linking region ($L_{II}$), and (c) a reactive region ($L_{III}$). Hereinafter, a detailed description will be given of the multifunctional group ligand.

The "adhesive region ($L_I$)" means a portion of the multifunctional group ligand which contains a functional group capable of adhering to nanoparticles, and preferably an end of the ligand. Accordingly, it is preferable that the adhesive region include the functional group having a high affinity for a material constituting the nanoparticles, and the functional group of the adhesive region may be selected depending on the type of material constituting the nanoparticles. The adhesive region may include —COOH, —NH$_2$, —SH, —CONH$_2$, —PO$_3$H, —PO$_4$H, —SO$_3$H, —SO$_4$H, or —OH as the functional group.

The "cross-linking region (L$_{II}$)" means another portion of the multifunctional group ligand which includes a functional group capable of being cross-linked with neighboring multifunctional group ligands, and preferably the central portion of the ligand. "Cross-linking" means an intermolecular interaction between the adjacent multifunctional group ligands. Illustrative, but non-limiting, examples of the intermolecular interaction include a hydrophobic interaction, a hydrogen bond, a covalent bond (e.g. disulfide bond), a van der Waals bond, and an ionic bond. Since the intermolecular interaction is not limited to the above examples, the functional group to be cross-linked may be selected depending on the type of desired intermolecular interaction. The cross-linking region may include —SH, —NH$_2$, —COOH, —OH, -epoxy, -ethylene, or -acetylene as the functional group.

The "reactive region (L$_{III}$)" means another portion of the multifunctional group ligand which contains a functional group capable of adhering to an active component, and preferably the other end positioned opposite to the reactive region. The functional group of the reactive region depends on the type and chemical formula of active component (refer to Table 1). Non-limiting, illustrative examples of the functional groups of the reactive region include —SH, —COOH, —NH$_2$, —NH$_2$, —OH, —NR$_4^+$X$^-$, -sulfonate, -nitrate, or phosphonate.

ligand is dimercaptosuccinic acid. This is based on the fact that dimercaptosuccinic acid originally includes an adhesive region, a cross-linking region, and a reactive region. In other words, —COOH located at one end of dimercaptosuccinic acid adheres to the nanoparticle, —SH positioned at the center of dimercaptosuccinic acid is bonded to neighboring dimercaptosuccinic acid by a disulfide bond, and —COOH and —SH located at the other end of dimercaptosuccinic acid are bonded to active components. In addition to dimercaptosuccinic acid, a compound, which includes —COOH as the functional group of the adhesive region (L$_I$), —SH as the functional group of the cross-linking region (L$_{II}$), and —COOH or —SH as the functional group of the reactive region (L$_{III}$), may be used as the preferred multifunctional group ligand. Illustrative, but non-limiting examples of the compound include dimercaptomaleic acid and dimercaptopentadionic acid.

In the water-soluble nanoparticles according to the present invention, another example of a preferred multifunctional group ligand is peptide. Peptide is an oligomer/polymer consisting of a few amino acids. Amino acid has —COOH and —NH$_2$ functional groups at both ends thereof, and thus, peptide spontaneously includes an adhesive region and a reactive region. Additionally, since some amino acids have —SH or —OH as a branched chain, peptide, which is produced so that the said amino acids are contained in a cross-linking region, may be used as the multifunctional group ligand in the present invention.

In the present invention, the multifunctional group ligand may be formed in combination with a biodegradable polymer. Examples of the biodegradable polymer include polyphosphazene, polylactide, polylactide-co-glycolide, polycaprolac-

TABLE 1

Examples of functional groups of the reactive region included in the multifunctional group ligand

| I | II | III |
|---|----|-----|
| R—NH$_2$ | R'—COOH | R—NHCO—R' |
| R—SH | R'—SH | R—SS—R |
| R—OH | R'-(epoxy group) | R—OCH$_2$C(OH)CH$_2$—R' |
| RH—NH$_2$ | R'-(epoxy group) | R—NHCH$_2$C(OH)CH$_2$—R' |
| R—SH | R'-(epoxy group) | R—SCH$_2$C(OH)CH$_2$—R' |
| R—NH$_2$ | R'—COH | R—N=CH—R' |
| R—NH$_2$ | R'—NCO | R—NHCONH—R' |
| R—NH$_2$ | R'—NCS | R—NHCSNH—R' |
| R—SH | R'—COCH$_2$ | R'—COCH$_2$S—R |
| R—SH | R'—O(C=O)X | R—OCH$_2$(C=O)O—R' |
| R-(aziridine group) | R'—SH | R—CH$_2$CH(NH$_2$)CH$_2$S—R' |
| R—CH=CH$_2$ | R'—SH | R—CH$_2$CHS—R' |
| R—OH | R'—NCO | R'—NHCOO—R |
| R—SH | R'—COCH$_2$X | R—SCH$_2$CO—R' |
| R—NH$_2$ | R'—CON$_3$ | R—NHCO—R' |
| R—COOH | R'—COOH | R—(C=O)O(C=O)—R' + H$_2$O |
| R—SH | R'—X | R—S—R' |
| R—NH$_2$ | R'CH$_2$C(NH$^{2+}$)OCH$_3$ | R—NHC(NH$^{2+}$)CH$_2$—R' |
| R—OP(O$^{2-}$)OH | R'—NH$_2$ | R—OP(O$^{2-}$)—NH—R' |
| R—CONHNH$_2$ | R'—COH | R—CONHN=CH—R' |
| R—NH$_2$ | R'—SH | R—NHCO(CH$_2$)$_2$SS—R' |

(I: the functional group of the reactive region of the multifunctional group ligand, II: active components, and III: examples of bonds formed by reaction of I with II)

In the present invention, a compound originally containing the above functional groups may be used as the water-soluble multifunctional group ligand. Alternatively, a compound which is modified or produced through a chemical reaction known in the art so as to include the above functional groups may be used as the multifunctional group ligand.

In the water-soluble nanoparticles according to the present invention, an example of a preferred multifunctional group tone, polyanhydride, polymaleic acid and derivatives thereof, polyalkylcyanoacrylate, polyhydroxybutylate, polycarbonate, polyorthoester, polyethylene glycol, poly-L-lycine, polyglycolide, polymethylmethacrylate, and polyvinylpyrrolidone.

Meanwhile, an "active component", which is to be bonded to the reactive region of the multifunctional group ligand according to the present invention, may be selected depending on the application of the water-soluble nanoparticles according to the present invention. Examples of the active component may include a bioactive component, a polymer, or an inorganic supporter.

Illustrative, but non-limiting, examples of the bioactive component include tissue-specific binding substances, such as an antigen, an antibody, RNA, DNA, hapten, avidin, streptavidin, protein A, protein G, lectin, selectin; and pharmaceutically active components, such as anticancer drugs, antibiotic drugs, hormones, hormone antagonists, interleukin, interferon, growth factors, tumor necrosis factors, endotoxin, lymphotoxin, urokinase, streptokinase, tissue plasminogen activators, protease inhibitors, alkyl phosphocholine, surfactants, cardiovascular pharmaceuticals, gastrointestinal pharmaceuticals, and neuro pharmaceuticals.

Examples of the polymer include polyphosphazene, polylactide, polylactide-co-glycolide, polycaprolactone, polyanhydride, polymaleic acid and derivatives thereof, polyalkylcyanoacrylate, polyhydroxybutylate, polycarbonate, polyorthoester, polyethylene glycol, poly-L-lycine, polyglycolide, polymethylmethacrylate, and polyvinylpyrrolidone.

Illustrative, but non-limiting examples of the inorganic supporter include silica ($SiO_2$), titania ($TiO_2$), indium tin oxide (ITO), a carbon material (nanotube, graphite, fullerene or the like), a semiconductor substrate (Si, GaAs, AlAs or the like), and a metal substrate (Au, Pt, Ag, Cu or the like).

A method of producing the water-soluble nanoparticles of the present invention includes (1) synthesizing water-insoluble nanoparticles in an organic solvent, (2) dissolving the water-insoluble nanoparticles in a first solvent and dissolving water-soluble multifunctional group ligands in a second solvent, (3) mixing the two solutions of the step (2) to substitute surfaces of the water-insoluble nanoparticles with the multifunctional group ligands, and dissolving a mixture in an aqueous solution to conduct a separation process, and (4) cross-linking the substituted multifunctional group ligands with each other.

The step (1) of the method relates to a process of producing the water-insoluble nanoparticles. The process of producing the water-insoluble nanoparticles according to the present invention includes adding a nanoparticle precursor to an organic solvent containing a surface stabilizer at 10-600° C., maintaining the resulting solution under temperature and time conditions suitable to make the desired water-insoluble nanoparticles to chemically react the nanoparticle precursor and thus grow the nanoparticles, and separating and purifying the water-insoluble nanoparticles.

Illustrative, but non-limiting, examples of the organic solvent include a benzene-based solvent (e.g. benzene, toluene, halobenzene or the like), a hydrocarbon solvent (e.g. octane, nonane, decane or the like), an ether-based solvent (e.g. benzyl ether, phenyl ether, hydrocarbon ether or the like), and a polymer solvent.

In the step (2) of the method, the nanoparticles produced in the preceding step are dissolved in the first solvent and the multifunctional group ligand is dissolved in the second solvent. Examples of the first solvent include a benzene-based solvent (e.g. benzene, toluene, halobenzene or the like), a hydrocarbon solvent (e.g. pentane, hexane, nonane, decane or the like), an ether-based solvent (e.g. benzyl ether, phenyl ether, hydrocarbon ether or the like), halohydrocarbon (e.g. methylene chloride, methane bromide or the like), alcohol (e.g. methanol, ethanol or the like), a sulfoxide-based solvent (e.g. dimethylsulfoxide or the like), and an amide-based solvent (e.g. dimethylform amide or the like). In addition to the solvents capable of being used as the first solvent, water may be used as the second solvent.

In the step (3) of the method, the two solutions are mixed with each other. In this step, the organic surface stabilizer of the water-insoluble nanoparticles is substituted with the water-soluble multifunctional group ligand (refer to FIG. 1). The nanoparticles having the water-soluble multifunctional group ligand substituted as described above can be separated using a typical method known in the art. Usually, since the water-soluble nanoparticles are generated as a precipitate, it is preferable to conduct the separation process using a centrifuge or by filtration. After the separation process, it is preferable to control the pH to 5 to 10 through a titration process so as to obtain the stably dispersed water-soluble nanoparticles.

In the step (4) of the method, the multifunctional group ligands are cross-linked with each other through some chemical reactions, thereby stabilizing the water-soluble nanoparticles. Illustrative, but non-limiting, examples of the chemical reaction for the cross-linking include an oxidation reaction (e.g. disulfide bond) and a reduction reaction, a cross-linking reaction using a molecule connector, and a hydrogen bond. The nanoparticles stabilized by the cross-linking are dispersed well under conditions of pH of 5 to 10 and a salt concentration of about 1 M or less without aggregation.

A better understanding of the present invention may be obtained through the following examples which are set forth to illustrate, but are not to be construed as the limit of, the present invention.

Example 1

Production of Iron Oxide Nanoparticles Having Various Sizes 4 nm iron oxide nanoparticles were synthesized by thermal decomposition of Iron triacetyl acetonate (Aldrich) in a phenylether solvent, which contains 0.3M lauric acid and 0.3M lauryl amine, at 260° C. for 1 hour. To synthesize 6 nm iron oxide nanoparticles, it had the same synthesis procedure as that of the 4 nm iron oxide nanoparticles except that benzyl ether was used as a solvent and a reaction temperature was 290° C. To produce 9 nm iron oxide nanoparticles, a benzyl ether solution, which contained 0.1 M lauric acid, 0.1 M lauryl amine, 8 mg/ml of 6 nm iron oxide nanoparticles, and iron triacetyl acetonate, was heated at 290° C. for 1 hour. The synthesis procedure of the 12 nm iron oxide nanoparticles was the same as that of the 9 nm iron oxide nanoparticles except that the 9 nm iron oxide nanoparticles were put in a solution in a concentration of 8 mg/ml.

Example 2

Figure 3:
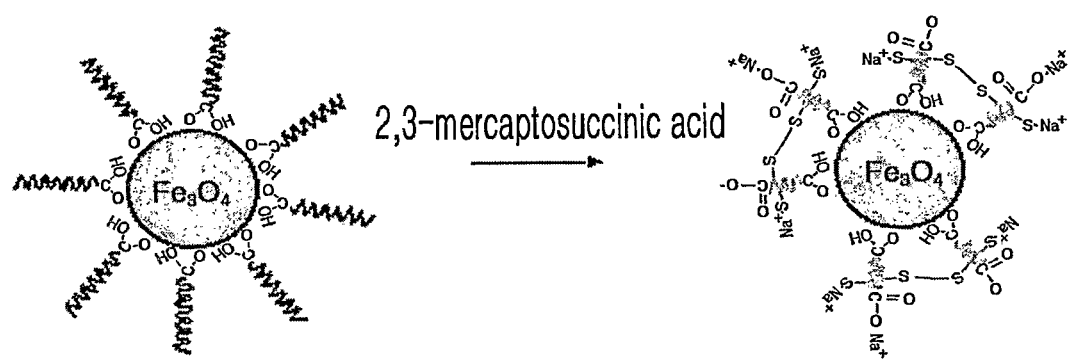
FIG. 3 illustrates the production process of water-soluble iron oxide nanoparticles surrounded by dimercaptosuccinic acid according to the present invention.

Production of Water-Soluble Iron Oxide Nanoparticles 5 mg of the iron oxide nanoparticles produced in example 1 were dissolved in 1 ml of toluene. Then 0.5 ml of methanol, in which 20 mg of 2,3-mercaptosuccinic acid was dissolved, was added to the above toluene solution (refer to FIG. 3). After about 24 hours, a dark brown precipitate was formed. The precipitate was centrifuged at room temperature at 2000 rpm for 5 min, and dispersed in 1 ml of deionized water. An air bubbling process was conducted for 5 min to achieve a disulfide bond of 2,3-mercaptosuccinic acid.

Example 3

Evaluation of Stability of Water-Soluble Iron Oxide Nanoparticles in an Aqueous Solution a. Analysis of Solubility of Water-Soluble Iron Oxide Nanoparticles The water-insoluble iron oxide nanoparticles produced in example 1 were dissolved in chloromethane, followed by the addition of water, whereas the water-soluble iron oxide nanoparticles produced in example 2 were dissolved in water, followed by the addition of chloromethane. Thereafter, a solubility variance caused by a surface substitution of the nanoparticles was analyzed.

Figure 4:
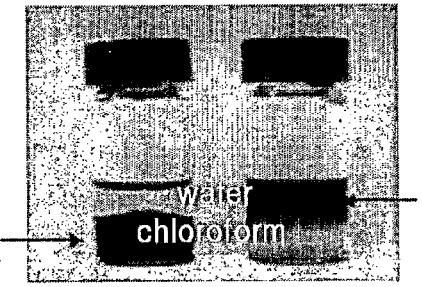
FIG. 4 illustrates the solubility of iron oxide nanoparticles, surrounded by an organic surface stabilizer, in an organic solvent, and the solubility of the water-soluble iron oxide nanoparticles, surrounded by water-soluble multifunctional group ligands, in an aqueous solution.

From FIG. 4, it was confirmed that a multifunctional group ligand (2,3-dimercaptosuccinic acid) was substituted with an organic surface stabilizer to convert water-insoluble nanoparticles into water-soluble nanoparticles. Additionally, it was confirmed through observation with the naked eyes that precipitation or aggregation did not occur, and thus, it can be seen that the water-soluble iron oxide nanoparticles are dispersed well in an aqueous solution.

b. Analysis Through Electrophoresis

10 μl of solution containing water-soluble iron oxide nanoparticles in a concentration of about 1 mg/ml was loaded in 1% agarose gel, and was subjected to an electrophoresis in a 1×TBE (tris-borate-edta) buffer solution while a voltage of 5 V/cm was applied to the resulting solution for 30 min.

Figure 5:
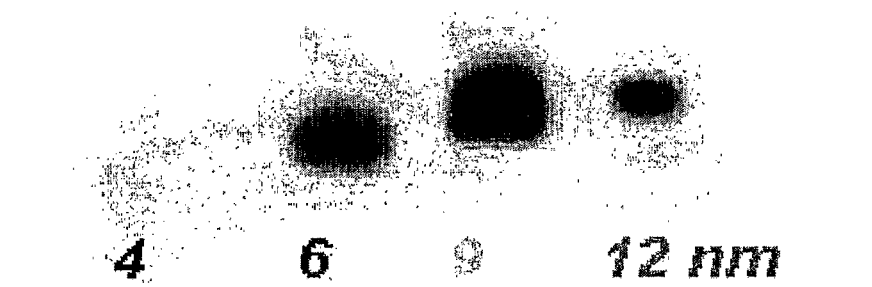
FIG. 5 illustrates the results of electrophoresis of the water-soluble iron oxide nanoparticles according to the present invention.
Figure 6A:
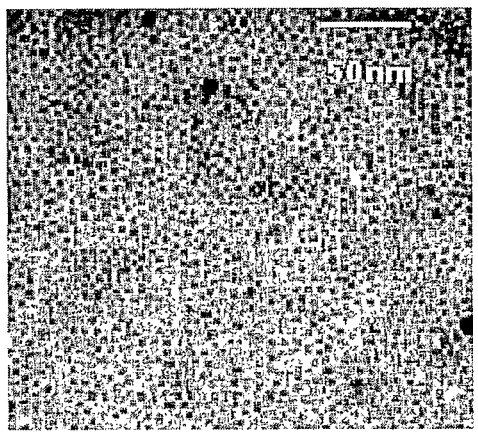
FIGS. 6A to 6D are transmission electron microscope (TEM) images of the water-soluble iron oxide nanoparticles (4, 6, 9, and 12 nm) according to the present invention.
Figure 6B:
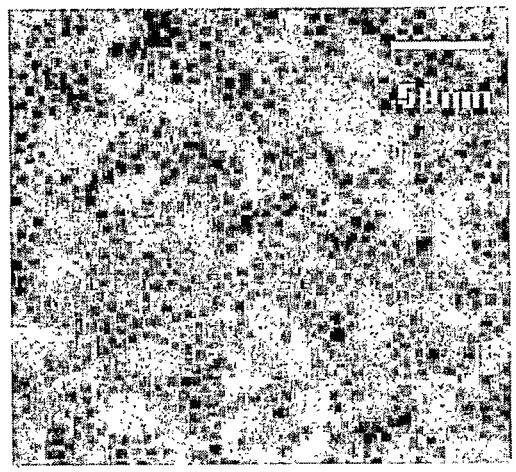
Figure 6C:
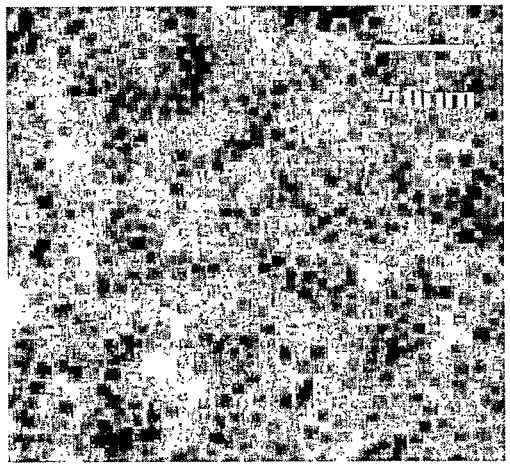
Figure 6D:
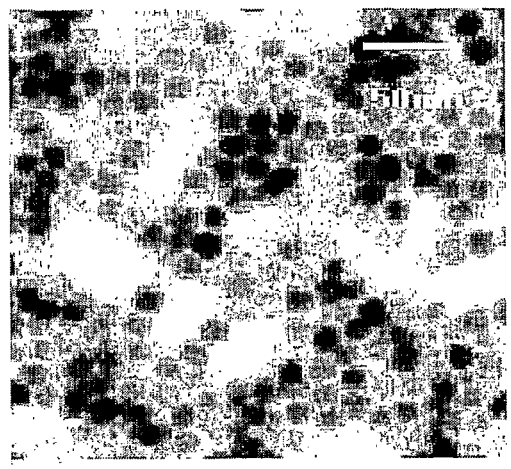

As shown in FIG. 5, water-soluble iron oxide nanoparticles moved through the gel since they were smaller than cavities formed in the agarose gel. Furthermore, a narrow band was formed on the gel, and thus, it can be seen that the water-soluble iron oxide nanoparticles were consistent in size and did not aggregate. Meanwhile, mobility was reduced in accordance with an increase in the size of the nanoparticles, which means that the water-soluble iron oxide nanoparticles were consistent in size and did not aggregate. Through the above results, it can be seen that the water-soluble iron oxide nanoparticles were dispersed in an aqueous solution, were consistent in size, and did not aggregate.

c. Analysis Using a Transmission Electron Microscope (TEM)

20 μl of solution containing water-soluble iron oxide nanoparticles were dropped on a TEM grid (Ted Pella Inc.) coated with a carbon film, dried for about 30 min, and observed using an electron microscope (EF-TEM, Zeiss, acceleration voltage 100 kV).

As shown in FIG. 6 the water-soluble iron oxide nanoparticles consistent in size were formed.

Example 4

Production of Core-Shell (FePt@$Fe_3O_4$) Nanoparticles 0.5 mmol Pt acetylacetonate was dissolved in 10 ml of benzylether, and heated to 100° C. 4 mmol oleic acid, 1.5 mmol Fe(CO)$_5$, and 4 mmol oleyl amine were added to the resulting benzylether, heated to 240° C., and maintained at that temperature for 1 hour to conduct a reaction. At this time, Fe(CO)$_5$ was decomposed. Subsequently, the resulting solution was heated to 300° C. and then maintained at that temperature for 1 hour. After the completion of the reaction, air was injected for 5 min to produce the core-shell (FePt@$Fe_3O_4$) nanoparticles.

Example 5

Production of Water-Soluble Core-Shell Nanoparticles

The water-soluble core-shell nanoparticles were produced by the same procedure as example 2 except that the core-shell nanoparticles produced through example 4 were used.

Example 6

Figure 7:
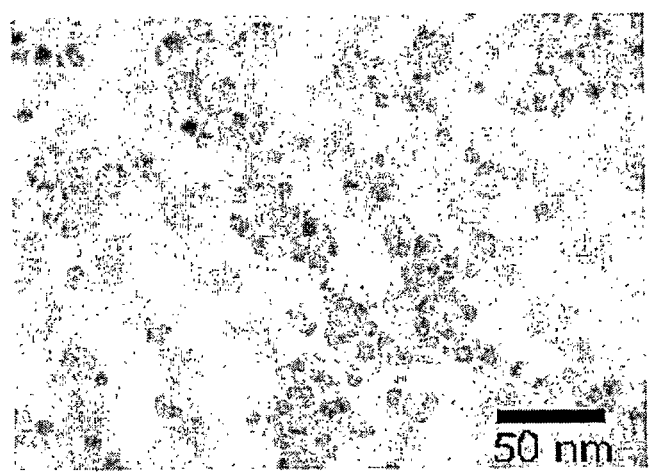
FIG. 7 illustrates the results of electrophoresis of the water-soluble core-shell (FePt@Fe$_3$O$_4$) nanoparticles according to the present invention.
Figure 7:
Figure 8:
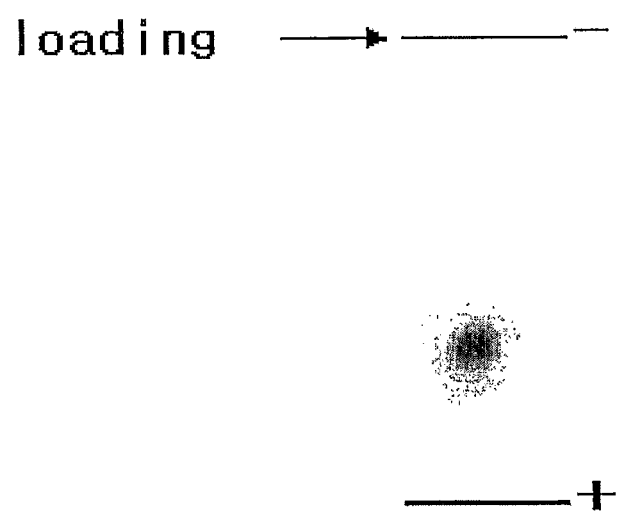
FIG. 8 is a transmission electron microscope (TEM) image of the water-soluble core-shell (FePt@Fe$_3$O$_4$) nanoparticles according to the present invention.

Evaluation of Stability of Water-Soluble Core-Shell Nanoparticles in an Aqueous Solution The stability of the water-soluble core-shell nanoparticles produced through example 5 in an aqueous solution was evaluated according to the same procedure as example 3 (refer to FIGS. 7 and 8).

Example 7

Production of Water-Soluble Iron Oxide Nanoparticles using Peptide as a Multifunctional Group Ligand The water-soluble iron oxide nanoparticles were produced through the same procedure of example 2 except that the following peptide was used instead of dimercaptosuccinic acid.

```
                                         SEQ ID No.: 1
     (1)      GSE SGG SG(Cha) CC(Cha) CDD -

SEQ ID No.: 2
     (2)      GRR SHG (Cha)CC (Cha)CD D -

SEQ ID No.: 3
     (3)      GKK HGH Y(Cha)C C(Cha)D CD -
     *Cha = cyclohexylalanine
```

Surfaces of the nanoparticles were substituted with peptide to produce nanoparticles that were stable in an aqueous solution. In peptide, a CDD or DCD portion containing —COOH acts as an adhesive region, a CC portion containing —SH acts as a cross-linking region, and the remaining portion acts as a reactive region.

Example 8

Production of Water-Soluble Iron Oxide Nanoparticles Combined with a tie2 Receptor Antibody as an Active Component 0.2 mg of tie2 receptor antibody was dissolved in 100 μl of 10 mM PBS (phosphate buffered saline, pH 7.2), and reacted with 20 μg of sulfo-SMCC (purchased from Pierce Inc.) for 30 min. Subsequently, the antibody combined with the sulfo-SMCC was separated through a gel filtration process (Sephadex G-25). The separated antibody reacted with 0.2 mg of water-soluble iron oxide nanoparticles produced through example 2 for 12 hours, and water-soluble iron oxide nanoparticles combined with the tie2 receptor antibody were separated using a gel filtration column (Sephacryl S200, S400).

Example 9

Figure 9:
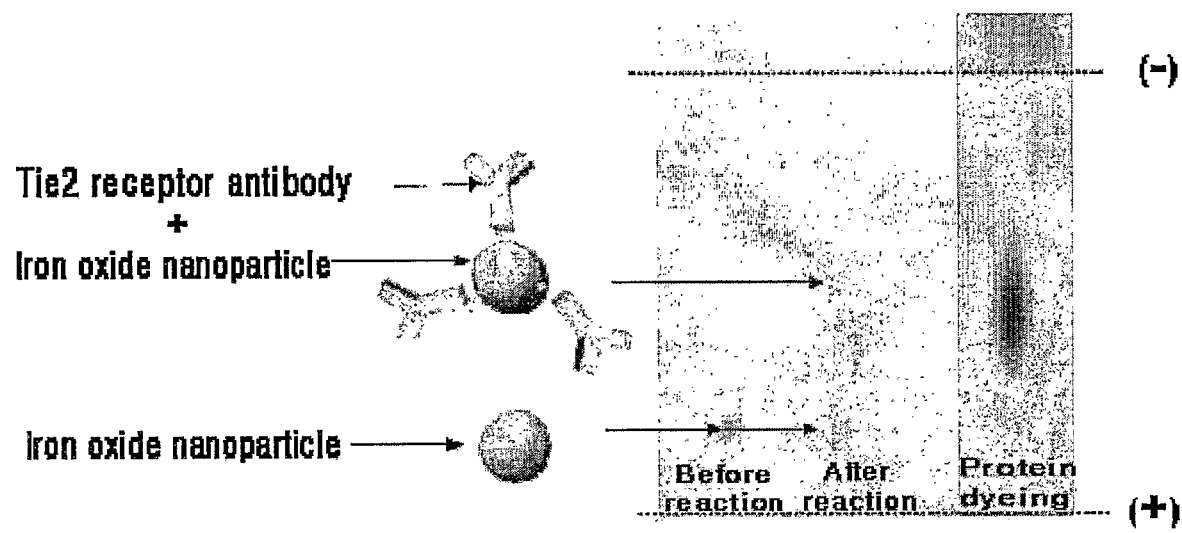
FIG. 9 illustrates the result of electrophoresis of the water-soluble iron oxide nanoparticles according to the present invention, which shows that the water-soluble iron oxide nanoparticles can be bonded to active components.

Confirmation of Combination of Water-Soluble Iron Oxide Nanoparticles with a tie2 Receptor Antibody The product of example 8 was subjected to an electrophoresis according to the same procedure as example 3, and the results are shown in FIG. 9.

FIG. 9 illustrates that a bioactive component (tie2 receptor antibody) can be bonded to a reactive region of the water-soluble nanoparticle. From the electrophoresis results, it can be seen that the iron oxide nanoparticle combined with the antibody has low movement during electrophoresis, which is similar to the results of a protein dyeing. Accordingly, it can be seen that the iron oxide nanoparticle is combined with the antibody.

INDUSTRIAL APPLICABILITY

Water-soluble nanoparticles according to the present invention are consistent in size, and are stable especially in aqueous solution. Accordingly, the nanoparticles employing various active components can be applied to composite material, electronic material, bio diagnosis, and treatment.

($L_I$), a cross-linking region ($L_{II}$), and a reactive region ($L_{III}$) which contains a functional group capable of adhering to an active component, in a second solvent;

(3) mixing two solutions in the step (2) to substitute organic surface stabilizers of the water-insoluble nanoparticles with the at least one water-soluble multifunctional group ligand and dissolving a mixture in an aqueous solution to conduct a separation process, wherein water-soluble nanoparticles are obtained; and (4) cross-linking the substituted multifunctional group ligands with each other on the water-soluble nanoparticles to stabilize the water-soluble nanoparticles;

wherein the water-soluble nanoparticles are each surrounded by multifunctional group ligands, and wherein the cross-linking region of the multifunctional group ligands is cross-linked with the cross-linking region of a neighboring multifunctional group ligand.

The invention claimed is:

1. A method of producing water-soluble nanoparticles, comprising:
   (1) synthesizing water-insoluble metal oxide nanoparticles in an organic solvent comprising an organic surface stabilizer by a thermal decomposition without using an oxidizing or a reducing agent;
   (2) dissolving the water-insoluble nanoparticles in a first solvent and dissolving at least one water-soluble multifunctional group ligand comprising an adhesive region 2. The method as set forth in claim 1, wherein the water-insoluble nanoparticles are produced according to a process which comprises adding the nanoparticle precursor to the organic solvent containing the surface stabilizer at 10-600° C., maintaining the resulting solvent under temperature and time conditions suitable for making the desired water-insoluble nanoparticles to chemically react the water-insoluble nanoparticle precursor and thus grow the nanoparticles, and separating and purifying the water-insoluble nanoparticles.

3. The method as set forth in claim 1, wherein the organic solvent is selected from the group consisting of a benzene-based solvent, a hydrocarbon solvent, an ether-based solvent, and a polymer solvent.

4. The method as set forth in claim 1, wherein the first solvent in the step (2) is selected from the group consisting of a benzene-based solvent, a hydrocarbon solvent, an ether-based solvent, halohydrocarbon, alcohol, a sulfoxide-based solvent, and an amide-based solvent.

5. The method as set forth in claim 1, wherein the second solvent in the step (2) is selected from the group consisting of a benzene-based solvent, a hydrocarbon solvent, an ether-based solvent, halohydrocarbon, alcohol, a sulfoxide-based solvent, an amide based solvent, and water.

6. The method as set forth in claim 1, wherein each of the water-soluble nanoparticles includes a metal, a metal chalcogenide, a magnetic material, a magnetic alloy, a semiconductor material, or a multicomponent mixed structure, and each of them has a diameter of 1-1000 nm.

7. The method as set forth in claim 6, wherein the metal is selected from the group consisting of Pt, Pd, Ag, Cu, Ru, Rh, Os and Au.

8. The method as set forth in claim 6, wherein the metal chalcogenide is selected from the group consisting of $M_xE_y$ (M=Ti, V, Cr, Mn, Fe, Co, Ni, Cu, Zr, Mo, Ru, Rh, Ag, W, Re, Ta, Zn; E=O, S, Se, $0<x\leq3$, $0\leq y\leq5$), $BaSr_xTi_{1-x}O_3$, $PbZr_xTi_{1-x}O_3$ ($0\leq x\leq1$), and $SiO_2$.

9. The method as set forth in claim 6, wherein the magnetic material is selected from the group consisting of Co, Mn, Fe, Ni, Gd, $MM'_2O_4$, $MxOy$ (M or M'=Co, Fe, Ni, Mn, Zn, Gd, Cr, $0<x\leq3$, $0\leq y\leq5$).

10. The method as set forth in claim 6, wherein the magnetic alloy is selected from the group consisting of CoCu, CoPt, FePt, CoSm, CoAu, CoAg, CoPtAu, CoPtAg, NiFe and NiFeCo.

11. The method as set forth in claim 6, wherein the semiconductor material is a first semiconductor material consisting of an element selected from a group II and an element selected from a group VI, a second semiconductor material consisting of an element selected from a group III and an element selected from a group V, a third semiconductor material consisting of a group IV, a fourth semiconductor material consisting of an element selected from the group IV and an element selected from the group VI, or a fifth semiconductor material consisting of an element selected from the group V and an element selected from the group VI.

12. The method as set forth in claim 6, wherein the multicomponent mixed structure includes two or more components selected from the group consisting of the metal, the metal chalcogenide, the magnetic material, the magnetic alloy, and the semiconductor according to selected from the group of Pt, Pd, Ag, Cu, Ru, Rh, Os, and Au, and has a core-shell or bar code shape.

13. The method as set forth in claim 1, wherein the adhesive region ($L_I$) includes a functional group selected from the group consisting of —COOH, —$NH_2$, —SH, —$CONH_2$, $PO_3H$, —$PO_4H$, —$SO_3H$, —$SO_4H$, and —OH.

14. The method as set forth in claim 1, wherein the cross-linking region ($L_{II}$) includes a functional group selected from the group consisting of —SH, —$NH_2$, —COOH, —OH, epoxy, -ethylene, and -acetylene.

15. The method as set forth in claim 1, wherein the reactive region ($L_{III}$) includes a functional group selected from the group consisting of —SH, —COOH, —$NH_2$, —OH, —$NR_4^+$ $X^-$, -sulfonate, -nitrate, and phosphonate.

16. The method as set forth in claim 1, wherein the active component is selected from the group consisting of a bioactive component, a polymer, and an inorganic supporter.

17. The method as set forth in claim 16, wherein the bioactive component is selected from the group consisting of an antigen, an antibody, RNA, DNA, hapten, avidin, streptavidin, protein A, protein G, lectin, selectin, an anticancer drug, an antibiotic drug, a hormone, a hormone antagonist, interleukin, interferon, a growth factor, a tumor necrosis factor, endotoxin, lymphotoxin, urokinase, streptokinase, a tissue plasminogen activator, a protease inhibitor, alkyl phosphocholine, a component indicated by a radioactive isotope, a surfactant, a cardiovascular pharmaceutical, a gastrointestinal pharmaceutical, and a neuro pharmaceutical.

18. The method as set forth in claim 16, wherein the polymer is selected from the group consisting of polyphosphazene, polylactide, polylactide-co-glycolide, polycaprolactone, polyanhydride, polymaleic acid and derivatives thereof, polyalkylcyanoacrylate, polyhydroxybutylate, polycarbonate, polyorthoester, polyethylene glycol, poly-L-lycine, polyglycolide, polymethylmethacrylate, and polyvinylpyrolidone.

19. The method as set forth in claim 16, wherein the inorganic supporter is selected from the group consisting of silica ($SiO_2$), titania ($TiO_2$), indium tin oxide (ITO), a carbon material, a semiconductor substrate, and a metal substrate.

20. The method as set forth in claim 1, wherein the multifunctional group ligand is a peptide containing at least one amino acid having —SH, —COOH, —$NH_2$, or —OH as a branched chain.

21. A method of producing water-soluble nanoparticles, comprising:
(1) synthesizing water-insoluble nanoparticles in an organic solvent;
(2) dissolving the water-insoluble nanoparticles in a first solvent and dissolving at least one water-soluble multifunctional group ligand comprising an adhesive region ($L_I$), a cross-linking region ($L_{II}$), and a reactive region ($L_{III}$) which contains a functional group capable of adhering to an active component, in a second solvent;
(3) mixing two solutions in the step (2) to substitute surfaces of the water-insoluble nanoparticles with the at least one water-soluble multifunctional group ligand and dissolving a mixture in an aqueous solution to conduct a separation process; and
(4) cross-linking the substituted multifunctional group ligands with each other;
wherein the water-soluble nanoparticles are each surrounded by multifunctional group ligands, and wherein the cross-linking region of the multifunctional group ligands is cross-linked with the cross-linking region of a neighboring multifunctional group ligand,
wherein the water-soluble multifunctional group ligand is a peptide containing any one of amino acid sequences described in SEQ ID Nos. 1 to 3.

22. The method as set forth in claim 1, wherein the multifunctional group ligand is a compound, which includes —COOH as a functional group of the adhesive region ($L_I$), —SH as a functional group of the cross-linking region ($L_{II}$), and —COOH or —SH as a functional group of the reactive region ($L_{III}$).

23. The method as set forth in claim 22, wherein the compound is selected from the group consisting of dimercaptosuccinic acid, dimercaptomaleic acid, and dimercaptopentadionic acid.

24. The method as set forth in claim 1, wherein the multifunctional group ligand is combined with a biodegradable polymer.

25. The method as set forth in claim 24, wherein the biodegradable polymer is selected from the group consisting of polyphosphazene, polylactide, polylactide-co-glycolide, polycaprolactone, polyanhydride, polymaleic acid and derivatives thereof, polyalkylcyanoacrylate, polyhydroxybutylate, polycarbonate, polyorthoester, polyethylene glycol, poly-L-lycine, polyglycolide, polymethylmethacrylate, and polyvinylpyrrolidone.

* * * * *

```
SEQUENCE LISTING

<160> NUMBER OF SEQ ID NOS: 3

<210> SEQ ID NO 1
<211> LENGTH: 15
<212> TYPE: PRT
<213> ORGANISM: Artificial  Sequence
<220> FEATURE:
<223> OTHER INFORMATION: multi-functional  group  ligand:  9th  and
      12th  Ala  are  cyclohexylalanine

<400> SEQUENCE: 1

Gly Ser Glu Ser Gly Gly Ser Gly Ala Cys Cys Ala Cys Asp Asp
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: multi-functional  group  ligand:  7th  and
      10th  Ala  are  cyclohexylalanine

<400> SEQUENCE: 2

Gly Arg Arg Ser His Gly Ala Cys Cys Ala Cys Asp Asp
1               5                   10

<210> SEQ ID NO 3
<211> LENGTH: 14
<212> TYPE: PRT
<213> ORGANISM: Artificial Sequence
<220> FEATURE:
<223> OTHER INFORMATION: multi-functional  group  ligand:  8th  and
      11th  Ala  are  cyclohexylalanine

<400> SEQUENCE: 3

Gly Lys Lys His Gly His Tyr Ala Cys Cys Ala Asp Cys Asp
1               5                   10
```